United States Patent [19]

Löhn

[11] 4,227,878
[45] Oct. 14, 1980

[54] DENTAL HANDPIECE

[75] Inventor: Gerd Löhn, Biberach, Fed. Rep. of Germany

[73] Assignee: Kaltenbach & Voigt GmbH, Biberach, Fed. Rep. of Germany

[21] Appl. No.: 881,565

[22] Filed: Feb. 27, 1978

[30] Foreign Application Priority Data

Mar. 19, 1977 [DE] Fed. Rep. of Germany ... 7707816[U]

[51] Int. Cl.³ .............................................. A61G 17/02
[52] U.S. Cl. ................................................... 433/80
[58] Field of Search ............... 251/321, 335 A; 32/22, 32/66; 128/240, 241, 224

[56] References Cited

U.S. PATENT DOCUMENTS

| 2,083,156 | 6/1937 | McCabe | 251/321 |
| 2,195,554 | 4/1940 | Beardsley | 251/321 |
| 2,550,863 | 5/1951 | Roehr | 251/321 |
| 2,723,055 | 11/1955 | Beard, Jr. | 251/321 |
| 3,698,088 | 10/1972 | Austin, Jr. | 32/22 |

Primary Examiner—Robert Peshock
Attorney, Agent, or Firm—Scully, Scott, Murphy & Presser

[57] ABSTRACT

A dental handpiece for dispensing liquid and/or gaseous media into the mouth of a patient and having one or more internal ducts for supplying the media to a dispensing outlet. A shut-off valve is provided in each duct and comprises a valve seat, a closure body engaging the valve seat, and a plunger operable from externally of the handpiece to lift-off the closure body from the valve seat. An external actuator button is moveable in a radial aperture in the handpiece and is coupled with the plunger in a sealed valve chamber. When the plunger lifts-off the closure body from the valve seat, fluid medium can pass from the supply duct through the valve seat and the valve chamber to a duct leading to the dispensing outlet. The actuator button can be manipulated up and down in the aperture, but it can also carry out lateral tilting movement in order to operate the plunger. The enable the tilting movement, the actuator button has lateral clearance in the aperture, and also the cross-section of the valve chamber into which the button or its stem extends is at least as large as the cross-section of the aperture.

15 Claims, 4 Drawing Figures

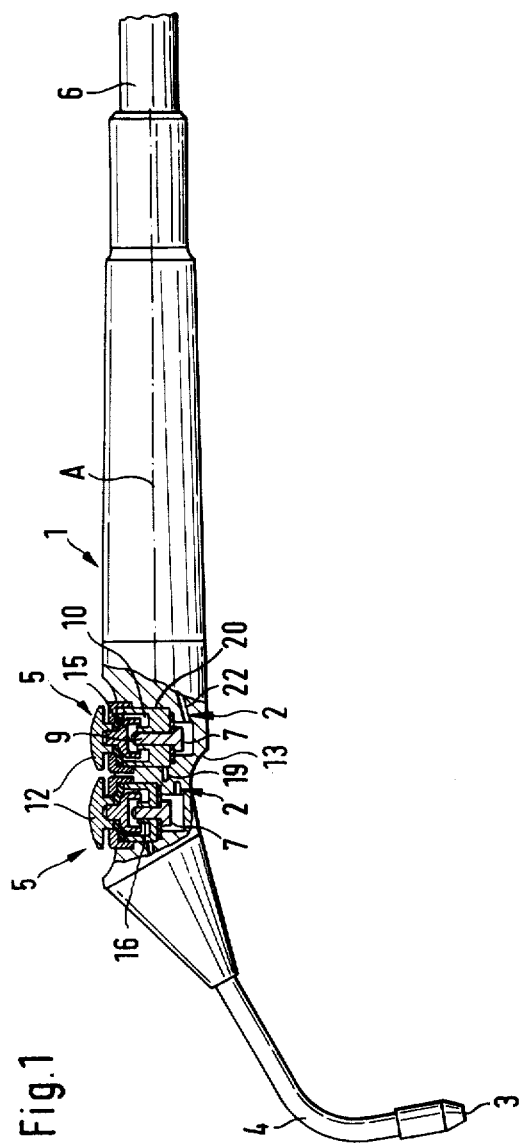

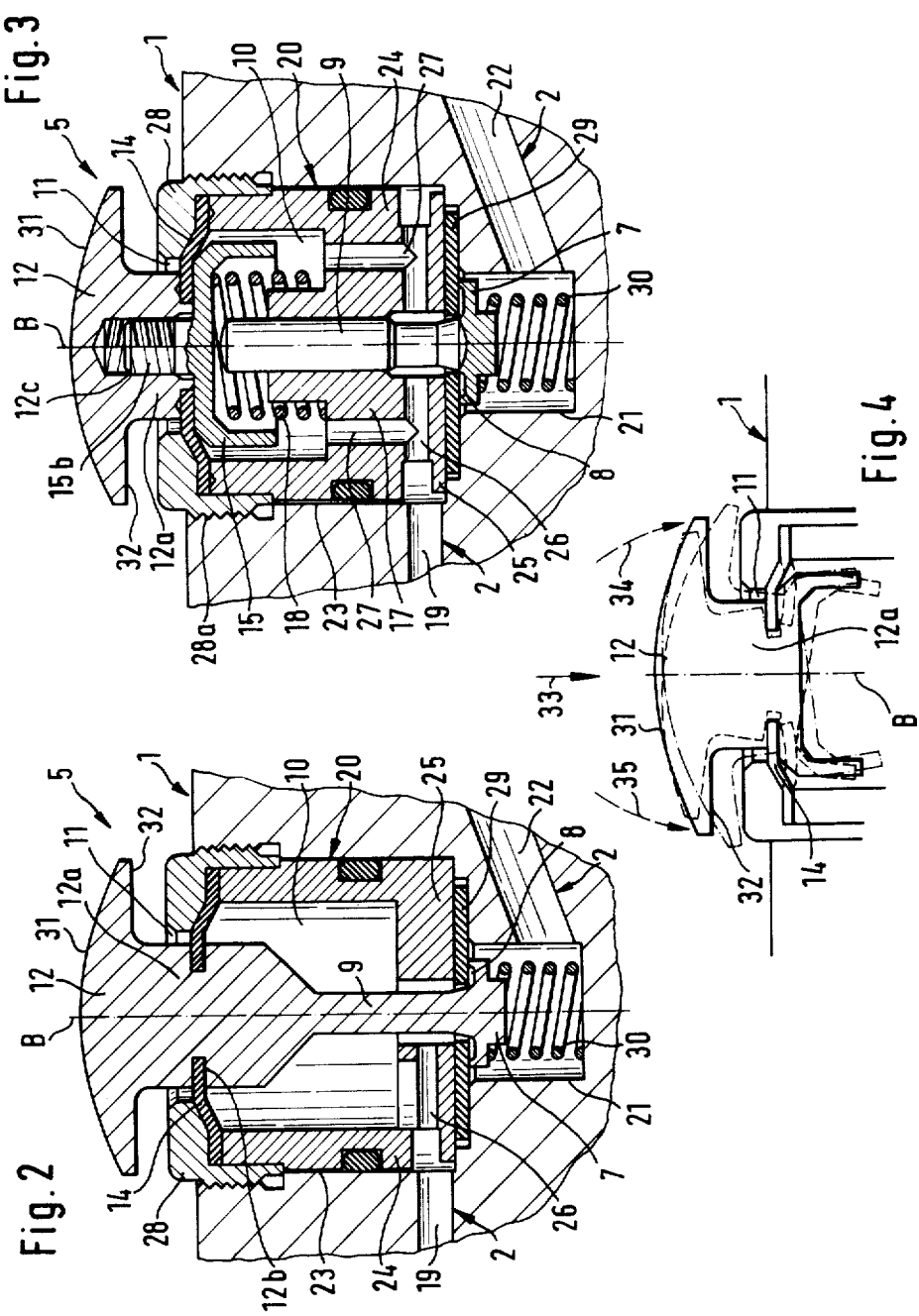

DENTAL HANDPIECE

This invention relates to a dental handpiece for dispensing at least one fluid medium, such as air and/or water, and comprising; a supply duct extending within the handpiece for supplying a fluid medium to a dispensing outlet; a shut-off valve provided in the handpiece for controlling the supply of fluid medium from the supply duct to the dispensing outlet, the valve comprising a valve seat, a closure body moveable between open and closed positions relative to the valve seat, and a plunger operable from externally of the handpiece to move the closure body from the closed position to the open position; a valve actuator accessible from externally of the handpiece and coupled with the plunger; a transverse aperture provided in the handpiece, the valve actuator extending through the aperture; and a valve chamber communicating with the dispensing outlet and being communicable with the supply duct via the valve seat when the closure body is in its open position, the valve chamber receiving the plunger and being sealed against loss of fluid medium to the exterior of the handpiece via the transverse aperture.

The handpieces serve for guiding into the oral cavity of a patient, during tooth treatment, a drying, cooling or cleaning medium, which may optionally be heated, for example air and/or water. For this purpose, the handpiece is connected to a flexible supply hose connected at the one end to a source of the medium under pressure and at the other end to the medium supply duct arranged in the handpiece. Frequently there are arranged in the handpiece two medium supply ducts each having a shut-off valve, for example a supply duct for air and a supply duct for water, each shut-off valve having its own valve actuating knob. In this manner, the handpiece constitutes a so-called triple function syringe the first function of which, on actuating one of the knobs, is the dispensing of air, the second function of which, on actuating the other knob, is the dispensing of water and the third function of which, on jointly actuating the two knobs arranged in juxtaposition, is the dispensing of an air-water mixture.

A dental handpiece of the above type is known from German Offenlegungsschrift No. 24 33 819. In the case of this known handpiece, the valve actuating knob is rigidly connected to the valve plunger and is guided without clearance in transverse (radial) aperture and can therefore only be actuated by axial pressure coinciding with the axis of the valve plunger, the valve plunger being also guided without clearance through a bush secured in the handpiece in the valve chamber and having, at its end remote from the actuating knob, the valve seat for the valve closure body arranged rearwardly thereof, the actuating knob being secured against falling out of the radial aperture.

It is the result of the lack of clearance that the dentist or assistant is required always to grasp the handpiece with a pre-determined hand position so as then, in an aimed manner, to be able to exert with the finger the necessary axial pressure on the valve actuating knob.

Since, in the case of the known handpiece, the valve actuating knobs are arranged in an oblique face at the end of the handpiece remote from the supply hose end of the handpiece and since, as is conventional, a hollow needle provided with the dispensing aperture extends from this end, the dentist is compelled always to hold the handpiece with four fingers of the hollow hand, the hollow needle being directed in pistol-like manner away from the hand. Only this pre-determined holding by the hand in the manner of the grasping of a pistol makes it possible for the dentist to exert the aforementioned axial pressure on the valve actuating knob or knobs, for which purpose solely the thumb can be used, and this represents a limitation of the manipulation possibilities.

It is an object of the invention to obviate these disadvantages and to provide a dental handpiece which can be grasped with almost any optional arrangement of the hand and nevertheless, independently of the arrangement of the hand, permits sensitive and ready actuation of the valve actuator.

According to the invention, there is provided a dental handpiece for dispensing at least one fluid medium and comprising:

- a supply duct extending within the handpiece for supplying a fluid medium to a dispensing outlet;
- a shut-off valve provided in the handpiece for controlling the supply of fluid medium from the supply duct to the dispensing outlet, the valve comprising a valve seat, a closure body moveable between open and closed positions relative to said valve seat, and a plunger operable from externally of the handpiece to move the closure body from the closed position to the open position;
- a valve actuator accessible from externally of the handpiece and coupled with said plunger;
- a transverse aperture provided in said handpiece, said valve actuator extending through said aperture;
- and a valve chamber communicating with said dispensing outlet and being communicable with said supply duct via said valve seat when said closure body is in its open position, the said valve chamber receiving said plunger and being sealed against loss of fluid medium to the exterior of the handpiece via said transverse aperture;
- in which the valve actuator extends with clearance through said aperture into said valve chamber, and is moveable relative to said aperture and to said valve chamber in order to move said closure body to its open position via said plunger;
- and in which the cross-section of at least that part of said valve chamber in which the valve actuator is moveable is at least as large as the cross-section of said aperture.

It has been found, in surprising manner, with the design proposed, that even a relatively slight degree of clearance between the transverse, preferably radial aperture and the valve actuator e.g. a knob or, in the appropriate case, the stem of the knob is sufficient to enable the actuating knob to be actuated in, to a certain extent freely moveable manner, with a finger or a thumb in the sense of a tilting movement of the knob and, consequently, due to the force component triggered thereby and acting in the direction of the axis of the valve plunger, to lift at least partially the closure body from the valve seat, so that the shut-off valve is opened. Due to the possibility for actuating the valve actuating knob not only by direct axial pressure but also due to lateral pressure (i.e. by tilting), the essential advantage is achieved that the dentist or the assistant can grasp the handpiece not merely in the manner of grasping a pistol but also with any desired other posture of the hand, for example with the manner of holding by hand conventional for dental drilling handpieces, as if a pencil were being grasped, or also with all five fingers and with a to some extent transverse grasping movement. With this arrangement and in every case, actuation of the valve actuating knob is possible in simple manner, for example in the case of pencil grasped by means of the index finger, middle finger or ring finger and in the case of transverse embracing with all five fingers, in particular by the thumb, expediently with the outer portion of the thumb. The handpiece can also be braced in the manner of a whip grasping movement with the four fingers of one hand, the thumb bearing at the peripheral zone of the handpiece located opposite the actuating knob or knobs. In this case, the actuating knob can also readily be actuated with the index finger, middle or ring finger. Expediently, with this arrangement, there is arranged at the peripheral zone of the handpiece located opposite the valve actuating knob or knobs a finger supporting trough for the thumb.

The ready mode of actuation described, both in the sense of an axial movement and also in particular in the sense of a tilting movement of the valve actuating knob is not only independent of the hand positioning applied in each particular instance on grasping the handpiece and during the extraction following thereof of the same out of a handpiece retaining arrangement arranged at the dental apparatus stand, but also substantially independently of the location of the arrangement of the actuating knob or knobs at the handpiece. It has also been found to be expedient that, in particular if there are two actuating knobs provided, the latter are arranged in juxtaposition in the direction of the axis of the elongate handpiece. The dentist or the assistant can then, in the easy manner mentioned and without looking towards them, i.e. by simple feel, jointly actuate the one, or the other, or both actuating knobs.

In every case, i.e. on actuating the valve actuating knob or button by axial pressure alone or by tilting, the actuating knob again recovers its starting position, in which the shut-off valve is closed, after termination of its actuation in consequence of the pressure exerted by the pressure medium building-up on the valve closure body and therewith, via the valve plunger, on itself. However, a supplementary restoring element may be provided by an arrangement whereby the valve actuating knob and/or the valve plunger is supported transversely of the axis of the valve plunger by a resilient supporting element relative to the handpiece or relative to a valve housing arranged in the handpiece. This biased resilient supporting element may be constituted for example by a resilient spoke arrangement or, for simultaneous sealing of the valve towards the exterior, by an annular membrane surrounding the valve actuating knob or the stem thereof and/or the valve plunger. In every case, the resilient support element provides, due to its bias, for restoring of the actuating knob, or it assists in such restoring.

One preferred embodiment of shut-off valve for achieving ready manipulation of the handpiece and ready actuation of the valve actuating knob is characterised in that the valve closure body, the valve plunger and the valve actuating knob are designed in their entirely as a one-piece unit, the valve plunger extending through the valve seat (constituting a through-passage for the medium) and the valve closure body being arranged on the side of the valve seat remote from the valve plunger, with which arrangement the valve chamber and also the valve seat having a cross-section permitting tilting of the one-piece unit, i.e. a correspondingly larger cross-section.

A further preferred embodiment consists in that the valve actuating knob has a prolongation or lower portion thereof projecting into the valve chamber and the resilient support element is inserted under stress between the actuating knob and the prolongation, the valve chamber having a larger cross-section than the radial passage and the resilient support element being fixed at or in the walls of the valve chamber, the prolongation having a larger cross-section than the radial aperture or passage and bearing under pressure against the resilient support element bearing at the inner rim of the radial aperture, so that the prolongation, and therewith the valve actuating knob, is secured against release from the valve interior.

Expediently, the prolongation is releasably connected with the valve actuating knob, for example by screwing-in a pin of the prolongation into a blind aperture formed in the actuating knob.

Especially ready operation during the actuation of the valve actuating knob may be effected by tilting if the valve plunger bears loosely against the prolongation.

With this arrangement, the valve plunger can be guided in a guiding bush arranged in the valve chamber of a valve element secured in the handpiece, it being possible to provide a supplementary recall element for the actuating knob and compression spring bearing at one end against the prolongation and at its other end against the valve element.

A further preferred development of the handpiece which is advantageous with regard to the fore-said easy running during tipping of the actuating knob, in the case of a shut-off valve arranged in a valve housing, is characterised in that the handpiece has a radially debouching chamber in the base zone of which (having a constricted cross-section) the arriving section of the medium supply duct terminates and in the main zone having a widened cross-section of which above this location there is inserted a valve housing designed in can-like or pot-like manner and in the base of which there is arranged the valve seat having a through passage for the medium and which in the open position of the valve is connected via an outlet duct of the valve housing with a section of the medium supply duct extending away to the dispensing aperture, the valve closure body having a larger cross-section than the valve seat and being arranged below the valve seat in the base zone of the chamber, and furthermore the outlet duct being connected via a connecting duct of the valve housing with the valve chamber (constituting a suction chamber upon release of the actuating knob) and in which there is arranged a guide bush for the valve plunger extending through the valve seat to a point of abutment against the valve closure body, the valve housing being sealed furthermore by a cover having the radial passage for the valve actuating knob and which constitutes a fixing element for the resilient support element (designed as a sealing membrane) which is secured between the rim of the valve housing and the cover and secured at the handpiece, for example by screwing. After release of the valve actuating knob and upon application of the valve closure body against the valve seat, the sealing membrane travels back into its starting position, whereby any liquid building-up in the section of the medium supply duct extending to the dispensing aperture is sucked back into the valve chamber (constituting a suction chamber as referred to above), so that in the mouth of the liquid dispensing aperture there is no longer any liquid available such as might be entrained in undesirable manner when for example drying a tooth, on subsequent dispensing of air out of the dispensing aperture provided for this purpose and surrounding the liquid dispensing aperture, for example concentrically.

The valve closure body may be retained in the closed position against the valve seat solely due to the pressure of the medium building-up in the base zone of the chamber, or there may be provided for this purpose a spring acting on the closure body to close the valve and which is designed as a compression spring and which may be arranged in the base zone of the chamber of constricted cross-section.

It is expedient if the actuating knob or button has an external head which is mushroom-shaped and which has a larger cross-section than the radial aperture, there being provided, between the underside of the head facing the handpiece and the handpiece or the cover of the valve housing, a degree of spacing permitting tipping of the valve actuating knob. Thereby, there is provided a stop limiting the tipping movement of the valve actuating knob, inasmuch as on tipping the actuating knob the mushroom underside passes into abutment at the handpiece or at the cover of the valve housing.

BRIEF DESCRIPTION OF THE DRAWINGS

FIG. 1 is a side view, partly in section, of an elongate dental handpiece according to the invention;

FIG. 2 is a detail sectional view of a first type of shut-off valve for use in the handpiece;

FIG. 3 is a detail sectional view of a second type of shut-off valve for use in the handpiece; and FIG. 4 illustrates different modes of operation of the shut-off valves.

DESCRIPTION OF THE PREFERRED EMBODIMENTS

Referring to FIG. 1, an elongate dental handpiece is provided with two fluid medium supply ducts 2 which extend within the interior of the handpiece to a concentric arrangement of dispensing apertures 3 (not shown in detail) at the end of a hollow needle 4 extending from one end of the handpiece at an angle to the general longitudinal axis A of the handpiece.

The handpiece is secured to a flexible supply hose 6 which, in a manner which is not shown, has two fluid medium supply lines, for example one for air and one for water, and which are connected to the supply ducts 2 in the handpiece 1. Provided in each medium supply duct 2 (according to FIG. 1) is a respective shut-off valve 5. The two shut-off valves 5 are arranged one behind the other with respect to the axis A of the handpiece 1.

A valve closure body 7 of each shut-off valve 5 is urged against a valve seat 8 (for example according to FIG. 1 under the pressure of the fluid medium building-up in the supply duct 2) in order to shut-off the supply of fluid medium to the respective aperture 3. The valve closure body 7 has associated with it a valve plunger 9 which is arranged in a valve chamber 10 that is sealed relative to the exterior. For actuating each valve plunger 9 there is provided a respective valve actuating knob 12 (or button) which can be manipulated from the exterior of the handpiece and which projects through a radial aperture 11 formed in the handpiece 1. For the purpose of opening the valve 5 by lifting-off of the closure body 7 from the valve seat 8, the knob 12 is depressed against the closure pressure acting on the body 7. The valve actuating knob 12 is (as will be clear also from the subsequent embodiments) secured against unintentional release from the interior of the valve.

As seen particularly in FIGS. 2 to 4, the knob 12 or the stem 12a thereof projects with radial clearance through the radial aperture 11 of the handpiece 1 into the valve chamber 10 (receiving the valve plunger 9), and the cross-section or diameter of chamber 10 is at least as large as the cross-section or diameter of the radial aperture 11—in the case illustrated, larger than the cross-section or the diameter of the radial aperture 11. While the entire depth of the chamber 10 may have the size and shape as described above, it would suffice for only the upper part of the chamber 10 which accommodates the movement of the stem 12a to have such shape and size.

Provided on the periphery of the handpiece oppositely to the knobs 12 is a finger supporting trough 13 (see FIG. 1).

A first embodiment of shut-off valve 5 is shown in detail in FIG. 2, in which the valve closure body 7, the valve plunger 9 and the actuating knob 12 are in their entirety designed as a one-piece unit. With this arrangement, the valve plunger 9 extends through the valve seat 8, the closure body 7 being arranged on the side of the valve seat 9 remote from the plunger 9. The valve chamber 10 and also the valve seat 8 have such a cross-section as to permit tilting of the one-piece unit. In the case illustrated, the cross-section or diameter of the valve chamber 10 is larger than the cross-section or diameter of the valve plunger 9, and also of the stem 12a of the actuating knob 12.

The one-piece unit is, according to FIG. 2, restrained from moving relative to the handpiece 1 and transversely of the axis B of the unit by a resilient supporting element 14. In order also to seal the valve chamber 10, the resilient supporting element 14 may be constituted by an annular, biased diaphragm. This resilient diaphragm is, in the case of the embodiment according to FIG. 2, snap-fitted into an annular groove 12b formed in the actuating knob 12 or its stem 12a and, as subsequently described in connection with FIG. 3, inserted under tension in the side wall of the valve housing 24 which contains the individual elements of the valve 5.

A further embodiment of shut-off valve 5 is shown in FIG. 3, in which the actuating knob 12 has a prolongation or lower portion thereof 15 projecting into the valve chamber 10, the resilient support element 14 being secured between the knob 12 or the stem 12a thereof and the prolongation 15. For this purpose, the prolongation 15 has a pin 15b which projects into a threaded blind aperture formed in the actuating knob 12 and is screwed therein by means of a screwthread 12c which establishes a releasable connection between the prolongation 15 and the actuating knob 12. Furthermore, the valve chamber 10 also has a larger cross-section than the radial aperture 11, the resilient support element (afforded also in this case by a sealing, biased membrane) being secured at or in the walls of the valve chamber 10, as will be discussed in greater detail later.

The prolongation 15 has a larger cross-section than the radial aperture 11 and bears under pressure against the resilient support element 14 (which bears at the inner edge of the radial aperture 11). In this manner, it is guaranteed that on actuating the actuating knob 12 in the sense of tilting the latter, a tilting inclination of the actuating knob 12 can be effected relative to the axis B. Furthermore, thereby the prolongation 15 (and therewith the actuating knob 12 screwed to it) is secured against release from the interior of the valve. With this embodiment, the valve plunger 9 may bear loosely against the prolongation 15.

As is further apparent from FIG. 3, the valve plunger 9 is guided in a guide bush 16 arranged in the valve chamber 10 of a valve element 17 secured to the handpiece. Adjacent the resilient support element 14 (designed as a diaphragm) there is provided a supplementary restoring element for the actuating knob 12 in the form of a helical compression spring 18 bearing at one end against the prolongation 15 and at its other end against the valve element 17.

It will furthermore be apparent from FIG. 3 that an end section 22 of the supply duct 2 terminates in a radially extending chamber 20 via a constricted cross-section base zone 21. A pot-like valve housing 24 is inserted into a main zone 23 (having an enlarged cross-section) of the chamber 20 with its base 25 extending towards the base zone 21 of the chamber 20. Arranged in the base 25 of the valve housing 24 is the valve seat 8 which, in the open position of the valve 5, is connected via an outlet duct 26 of the valve housing 24 to a section 19 of the medium supply duct 2 extending towards the dispensing aperture 3. The valve closure body 7 (having a larger cross-section than the valve seat) is arranged, separate from the valve plunger 9, below the valve seat 8 in the base zone 21 of the chamber 20. The outlet duct 26 is connected, via one or more connecting ducts 27 in the valve housing 24, to the valve chamber 10 in which is arranged the guiding bush 16 for the valve plunger 9, which extends through the valve seat 8 into abutment against the valve closure body 7. The valve housing 24 is sealed by a cover 28 formed with the radial passage 11 for the actuating knob 12. The cover 28 is screwed to the handpiece 1 by means of a screwthread 28a, so that subsequent to release of the cover 28 the valve housing 24 and therewith the entire shut-off valve 5 can be extracted. The screwed-in cover 28 also forms a fixing element for the resilient support element 14 secured between the edge of the valve housing 24 and cover 28, so that subsequent to screwing-tight of the cover 28 the resilient support element 14 is also secured at its outer edge or rim. Subsequent to release of the actuating knob 12 and consequent application of the closure body 7 against the valve seat 8, the resilient support element 14 (operating as a diaphragm piston) is moved-back (outwardly) into its starting position, so that the valve chamber 10 acts as a suction chamber in such manner that any liquid present in the section 19 leading to the dispensing aperture 3 is sucked back into the valve chamber 10.

Provided below the base 25 of the valve housing 24, in the embodiments of FIGS. 2 and 3, is an annular packing 29 permitting through-passage of the valve plunger 9.

Per se, the closure body 7 can be retained in the closed position solely by the pressure of the fluid medium building-up in the base zone 21 of the chamber 20, i.e. in abutment against the valve seat 8. However, on once again switching-on the handpiece 1 after previous switching-off, i.e. subsequent to a previous pressureless condition, it may be that the closure body 7 will not be able to move upwardly against gravity from a position at or below the outlet of the section 22 of the medium supply duct 2. Therefore, since there may be the possibility of a failure in the movement of the closure body 7 into the closed position, there is arranged in the constricted base zone 21 of the chamber 20 a compression spring 30 acting on the closure body 7 to urge the latter against the valve seat 8 or against the packing 29.

The head 31 of the actuating knob 12 is located externally of the handpiece and is of mushroom-like design, having a larger cross-section than the radial aperture 11. With this arrangement, spacing is provided between the underside 31 of the head facing the handpiece 1, and the cover 28 of the valve housing 24. This spacing is sufficiently large that the actuating knob 12 is able to perform tilting movements about the axis B. Simultaneously, by this arrangement, there is provided a stop limiting the tilting movement of the actuating knob 12 when the underside 32 passes into abutment with the cover 28.

FIG. 4 shows a plurality of actuating possibilities for the actuating know 12. The arrow 33 shown in full line illustrates the application of a direct axial pressure in the direction of the axis B (which is the only possible mode of actuation of the handpiece known from German Offenlegungsschrift 24 33 819). The arrow 34 shown in broken line illustrates a tipping movement of the actuating knob 12 clockwise relative to the axis B, whereas the arrow 35 shown in dot-dash line illustrates a tilting movement of the actuating knob 12 relative to the axis B in anti-clockwise direction. The individual positions of the actuating knob 12 during the three modes of actuation mentioned are shown in the same manner as the three arrows 33, 34, 35.

I claim:

1. A dental syringe for dispensing at least one fluid medium and comprising:

a supply duct extending within the syringe for supplying a fluid medium to a dispensing outlet;

a shut-off valve provided in the syringe for controlling the supply of fluid medium from the supply duct to the dispensing outlet, the valve comprising a valve seat, a closure body moveable between open and closed positions relative to said valve seat and arranged to be biased to its closed position by the action of the closure body of fluid medium when the latter is supplied by said duct to said valve, and a plunger operable from externally of the syringe to move the closure body from the closed position to the open position;

a valve actuator accessible from externally of the syringe and coupled with said plunger, said valve actuator being coupled with said valve in such a way as to avoid unintentional removal of the valve actuator from the syringe;

said actuator being supported by a resilient support element arranged resiliently to resist movement in a direction transverse to the axis of said plunger;

a transverse aperture provided in said syringe, said valve actuator extending through said aperture;

and a valve chamber communicating with said dispensing outlet and being communicable with said supply duct via said valve seat when said closure body is in its open position, the said valve chamber receiving said plunger and being sealed against loss of fluid medium to the exterior of the handpiece via said transverse aperture, and the whole of said valve chamber having a cross-section which is at least as large as that of said transverse aperture;

said actuator having a lower portion extending from the main body of the actuator into said valve chamber, and said resilient support element being inserted under stress between the main body of said actuator and said lower portion, said valve chamber having a larger cross-section than that of said transverse aperture, and said resilient support element being fixed to the wall of said valve chamber, and said lower portion of the actuator having a larger cross-section than that of said transverse aperture and bearing under pressure against said resilient support element bearing at an inner rim of said transverse aperture;

in which the valve actuator extends with clearance through said aperture into said valve chamber, and is thereby moveable axially and by tilting relative to said aperture and to said valve chamber in order to move said closure body to its open position via said plunger;

and in which the cross-section of at least that part of said valve chamber in which the valve actuator is moveable is at least as large as the cross-section of said aperture.

2. A dental syringe according to claim 1 and having a plurality of fluid medium supply ducts, and a corresponding number of shut-off valves and valve actuators, in which each valve actuator includes an operating button, and the buttons of said actuators are arranged one behind the other with respect to the longitudinal axis of the handpiece.

3. A dental syringe according to claim 1, in which said closure body, said plunger and said actuator together form a one-piece unit, said plunger extending through said valve seat, said closure body being arranged on the side of the valve seat remote from said plunger, and said valve chamber and also said valve seat having a cross-section permitting tilting movement of said one-piece unit.

4. A dental syringe according to claim 1, in which at least one of said actuator and said plunger is supported by a resilient support element arranged resiliently to resist movement in a direction transverse to the axis of said plunger.

5. A dental syringe according to claim 4, in which said resilient support element comprises an annular membrane.

6. A dental syringe according to claim 1, in which said prolongation is releasably connected to said actuator.

7. A dental syringe according to claim 1, in which said plunger bears loosely against said prolongation.

8. A dental syringe according to claim 7, in which said plunger is guided in a guide bush of a valve element which is arranged in said valve chamber and is secured on the handpiece.

9. A dental syringe according to claim 8, including a restoring spring engaging at one end with said prolongation and at its other end with said valve element for urging said actuator outwardly relative to the handpiece.

10. A dental syringe according to claim 1 and further comprising:

a two-part radially extending chamber in said handpiece, a first part communicating with said duct and said second part being larger in cross-section than said first part;

a valve housing mounted in said second part, said housing being provided with said valve seat and with an outlet duct communicating with said duct section extending to said dispensing outlet, and said closure body having a larger cross-section than said valve seat and being positioned in said first part so as to allow the flow of fluid medium from the supply duct to the dispensing outlet when the closure body is in its open position;

a connecting duct provided in said valve housing and intercommunicating said outlet duct and said valve chamber;

a cover for said valve housing formed with said transverse aperture and serving to maintain said valve housing in said second part of the chamber;

a guide bush arranged in said second part of the chamber for guiding the movement of said plunger, the latter extending through said valve seat to engage at one end with said closure body and being engageable at its opposite end by said actuator;

and a sealing diaphragm held between said cover and said valve housing and serving both to seal said valve chamber and also to provide resilient lateral support to said actuator, said diaphragm being moveable by said actuator so as to reduce the volume of said valve chamber when said actuator is moved to lift said closure body from said valve seat via said plunger and said diaphragm being moveable to develop suction in said valve chamber upon release of said actuator whereby suction is applied to said dispensing outlet from said valve chamber via said connecting duct and said outlet duct.

11. A dental syringe according to claim 10, in which an annular packing is provided at one end of said valve housing and arranged to permit passage of said plunger and to seal said valve seat.

12. A dental syringe according to claim 1, including a spring engaging said closure body to urge the latter into engagement with said valve seat.

13. A dental syringe according to claim 12, in which said spring is a compression spring which is arranged in said first part of the chamber.

14. A dental syringe according to claim 1, in which said actuator has a head disposed externally of the handpiece, the head being mushroom-shaped and having a larger cross-section than that of said transverse aperture, and a space being provided betwen the underside of said head facing the handpiece and the handpiece which permits limited tilting of said head.

15. A dental syringe according to claim 1, in which said transverse aperture is a radial aperture.

* * * * *